United States Patent [19]

Naeder

[11] Patent Number: 5,062,859

[45] Date of Patent: Nov. 5, 1991

[54] PROSTHETIC FOOT HAVING Z SHAPED INSERT

[75] Inventor: Max Naeder, Duderstadt, Fed. Rep. of Germany

[73] Assignee: Otto Bock Orthopaedische Industrie Besitz- und Verwaltungs-Kommanditgesellschaft, Duderstadt, Fed. Rep. of Germany

[21] Appl. No.: 536,099

[22] Filed: Jun. 11, 1990

[30] Foreign Application Priority Data

Jun. 9, 1989 [DE] Fed. Rep. of Germany ....... 3918810

[51] Int. Cl.$^5$ ................................................. A61F 2/66
[52] U.S. Cl. ......................................... 623/55; 623/53
[58] Field of Search .................................... 623/53-56

[56] References Cited

U.S. PATENT DOCUMENTS

| 2,440,075 | 4/1948 | Campbell . | |
|---|---|---|---|
| 2,556,525 | 6/1951 | Drennon . | |
| 4,547,913 | 10/1985 | Phillips | 623/53 X |
| 4,645,509 | 2/1987 | Poggi et al. | 623/53 X |
| 4,718,913 | 1/1988 | Voisin | 623/49 |

FOREIGN PATENT DOCUMENTS

| 0331468 | 9/1989 | European Pat. Off. . | |
|---|---|---|---|
| 311463 | 7/1917 | Fed. Rep. of Germany . | |
| 0309066 | 11/1918 | Fed. Rep. of Germany | 623/53 |
| 325171 | 9/1920 | Fed. Rep. of Germany . | |
| 354246 | 6/1922 | Fed. Rep. of Germany . | |
| 1998183 | 11/1965 | Fed. Rep. of Germany . | |
| 0866907 | 9/1941 | France | 623/53 |
| 2293186 | 12/1974 | France . | |
| 2626463 | 8/1989 | France . | |
| WO88/00815 | 2/1988 | PCT Int'l Appl. | 623/55 |
| WO89/00035 | 1/1989 | PCT Int'l Appl. | 623/49 |

OTHER PUBLICATIONS

Stedman's Medical Dictionary, 1986.
Herkimer, "Engineers' Illustrated Thesaurus", 1952.
Van Nostrand's Scientific Encyclopedia, Sixth Edition, 1983.
E. Burges, et al., "Development and Preliminary Evaluation of the VA Seattle Foot", Journal of Rehabilitation Research and Development, vol. 22, No. 3, pp. 75-84.

Primary Examiner—David J. Isabella
Assistant Examiner—David H. Willse
Attorney, Agent, or Firm—Foley & Lardner

[57] ABSTRACT

A jointless prosthetic foot having a resilient foot insert, which is provided inside the prosthesis body, absorbs and transmits the prosthetic stresses, and which has a top horizontal section, forming the top edge of the prosthetic foot and offering a connection possibility with the prosthesis, and a bottom section which is of extended construction compared to the top section and extends with its free end into the toe region to achieve high elasticity for the front part of the foot in conjunction with high energy storage capacity when the front part of the foot is stressed, has at least a plantar flection and a dorsal flection, the top section and the bottom section enclosing a top and bottom angle respectively with the oblique Z-bar and delimiting rear and front wedge-shaped cavities respectively.

18 Claims, 7 Drawing Sheets

PROSTHETIC FOOT HAVING Z SHAPED INSERT

The invention relates to a jointless prosthetic foot having a resilient foot insert, which is provided inside the prosthesis body, absorbs and transmits the prosthetic stresses, and which has a top horizontal section, forming the top edge of the prosthetic foot and offering a connection possibility with the prosthesis, and a bottom section which is of extended construction compared to the top section and extends with its free end into the toe region to achieve a high degree of elasticity for the front part of the foot in conjunction with a high energy storage capacity when the front part of the foot is stressed.

A corresponding embodiment has become known as the so-called Seattle foot (see VETERANS ADMINISTRATION - JOURNAL OF REHABILITATION RESEARCH AND DEVELOPMENT, Vol.22, No.3, BPR 10-42, pages 75-84, in particular FIG. 6).

The function of a prosthetic foot depends substantially on its elastic properties. These are determined by material, design and arrangement of the elastic components used.

Depending on the intended area of application, which can range from normal walking on a level surface up to sporting use, such as jogging, running, jumping, depending on the desires of the amputee, the requirements of such components are widely varied, in particular as concerns their working capacity and the variation of their spring characteristics, closely associated with said working capacity, when stressed and unstressed.

The more recent developments of jointless prosthetic feet for as wide an area of application as possible deviate from the conventional concept of the SACH foot in that they supplement the rigid core of the foot in the front region of the foot with spring elements or replace it completely by such spring elements (e.g. SEATTLE foot) in order to improve the elasticity of the front part of the foot and thus also the energy storage capacity when the front part of the foot is stressed. In this case, the elasticity of the heel is achieved in a largely unchanged design by a foam wedge in the heel region.

The underlying object of the invention is to develop a prosthetic foot of the design explained above having improved properties.

According to the invention this object is achieved in that the foot insert, enabling at least plantar and dorsal flections as well as axial compression, has in the longitudinal section of the foot an approximately Z-shaped construction, the top section and the bottom section enclosing a top and bottom angle ($\alpha,\beta$) respectively with the oblique Z-bar and delimiting rear and front wedge-shaped cavities respectively.

In this case, it is advantageous if the top section of the foot insert can be twisted in its horizontal plane relative to the bottom section, that is to say to allow torsion about a vertical axis, and if, additionally, the top section of the foot insert can be twisted in the frontal plane lying transversely and perpendicular in relation to the direction of walking relative to the bottom section for adaptation to transverse inclinations in relation to the direction of walking.

According to the invention, it is possible for the resilient properties (spring characteristics), determining the force/path characteristic and the angle/moment characteristic of the swivel movements and deformations, to be solely determined by the Z-shaped foot insert. However, it is also possible for the spring characteristics to be achieved by interaction with the Z-shaped foot insert with additional resilient components which are arranged in at least one of the two wedge-shaped cavities.

According to the invention, it is basically possible for the foot insert to be of unstructured integral construction. However, according to the invention it can also be of two-part or three-part construction. The foot insert, or its individual members, can have a monostructure or a layered structure, e.g. such as a leaf spring structure, or can consist of a uniform material, or of several different materials. Even in a structured construction of the Z-shaped foot insert, this structure is not recognizable from the outside, with the result that the prosthetic foot according to the invention continues to provide the cosmetic advantages of a jointless foot.

The plantar flection is achieved by reducing the top angle $\alpha$ in a plane perpendicular to the pelvis and parallel to the direction of walking. The dorsal flection results by reducing the corresponding bottom angle $\beta$. A reduction in both angles $\alpha$ and $\beta$ leads to axial compression, that is to say to a deformation/movement perpendicular to the plane of the floor.

Movements in the sense of an enlargement of the angles $\alpha$ and/or $\beta$ are either delimited by the rigidity of the structure of the Z-shaped foot insert alone and/or by an additional device. This additional device can, for example, be a covering pulled onto the Z-shaped foot insert and of sock-like construction. However, mechanical stops and/or flexible straps or the like could also be provided.

According to the invention, all the functioning elements can be surrounded by foam in a foot shape and/or can be enclosed by a cosmetic cover.

The top horizontal section of the foot insert is designed in such a way that it offers a separate or integrated connection possibility with the prosthesis.

A special influence on the spring characteristics of the prosthetic foot can be achieved by the fact that separate or integrated support profiles are provided on the Z-shaped foot insert. These support profiles can be of hard or hard resilient construction and are preferably shaped in such a way that a contact point between two sections of the Z-shaped foot insert is displaced by said support profiles under increasing stress. In particular, the support profiles can be provided between the bottom section and the oblique Z-bar and constructed in such a way that they touch each other under stress and the contact point moves forwards under increasing stress so that the free length of spring available for the bottom section is shortened. By this means, a progessively harder spring characteristic results for the bottom horizontal section under increasing stress.

Further features of the invention are explained in greater detail in conjunction with further advantages of the invention with reference to exemplary embodiments.

Some embodiments of the invention serving as examples are illustrated diagrammatically in the drawings each in longitudinal section, in which.

Figure 1:
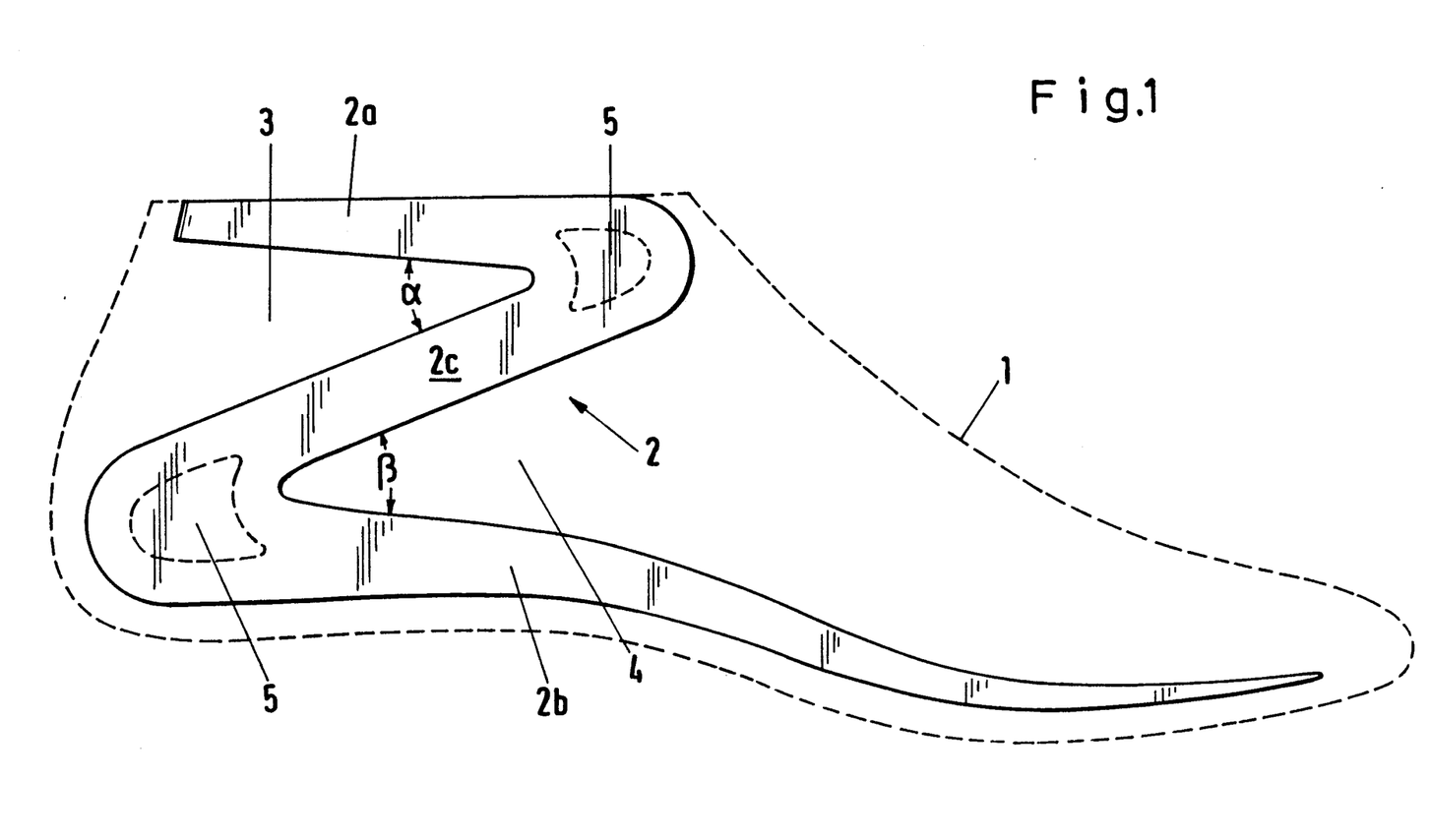
FIG. 1 shows a prosthetic foot having an unstructured integral foot insert.

FIG. 1 shows a jointless prosthetic foot having a resilient foot insert 2 which is provided inside a prosthesis body 1, illustrated in dashed lines, absorbs and transmits the prosthetic stresses, and which has in the longitudinal section of the foot an approximately Z-shaped construction. The top section 2a and the bottom section 2b enclose a top angle $\alpha$ and a bottom angle $\beta$ respectively with the oblique Z-bar 2c and delimit a rear wedge-shaped cavity 3 and a front wedge-shaped cavity 4. The top horizontal section 2a forms the top edge of the prosthetic foot and offers a connection possibility with the prosthesis (not illustrated in detail). The bottom section 2b is likewise aligned approximately horizontally, is of extended construction compared to the top section 2a, and extends with its free end into the toe region. Any inclination of the bottom section 2b results from the intended height of the heel.

The Z-shaped foot insert 2 results in high elasticity for the front part of the foot in conjunction with high energy storage capacity when the front part of the foot is stressed. Furthermore, the foot insert 2 allows plantar and dorsal flections as well as axial compression. Additionally, the top section 2a of the foot insert 2 can be twisted in its horizontal plane relative to the bottom section 2b. That is to say, it allows torsion about a vertical axis. Additionally, the top section 2a can be twisted in the frontal plane lying transversely and perpendicular in relation to the direction of walking relative to the bottom section 2b which results in an adaptation to transverse inclinations in relation to the direction of walking. The bottom profile of the bottom horizontal section 2b is adapted to be the profile of the underside of the foot.

The regions 5 drawn in dashed lines indicate cavities which can be provided to avoid additional material.

Figure 2:
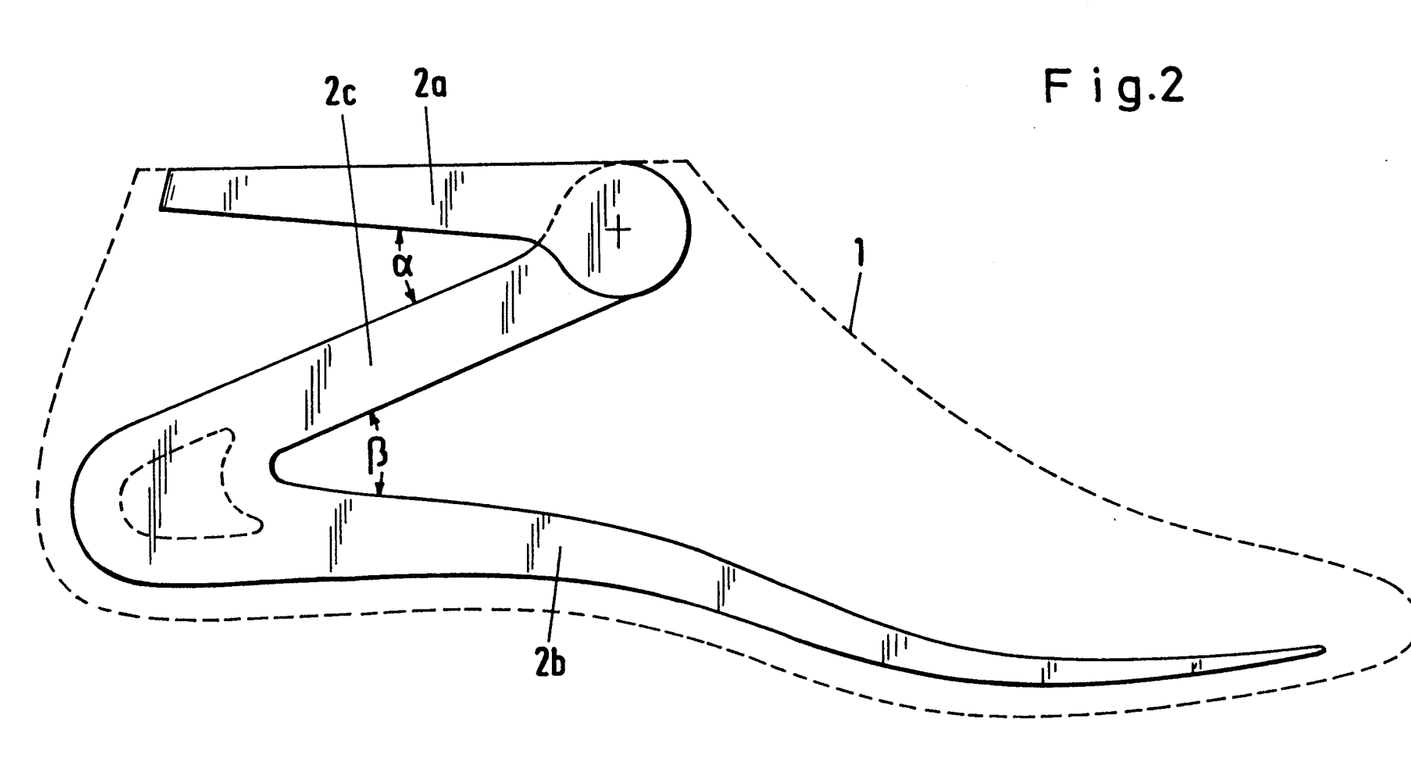
FIG. 2 shows a prosthetic foot having a foot insert of two-part construction.
Figure 3:
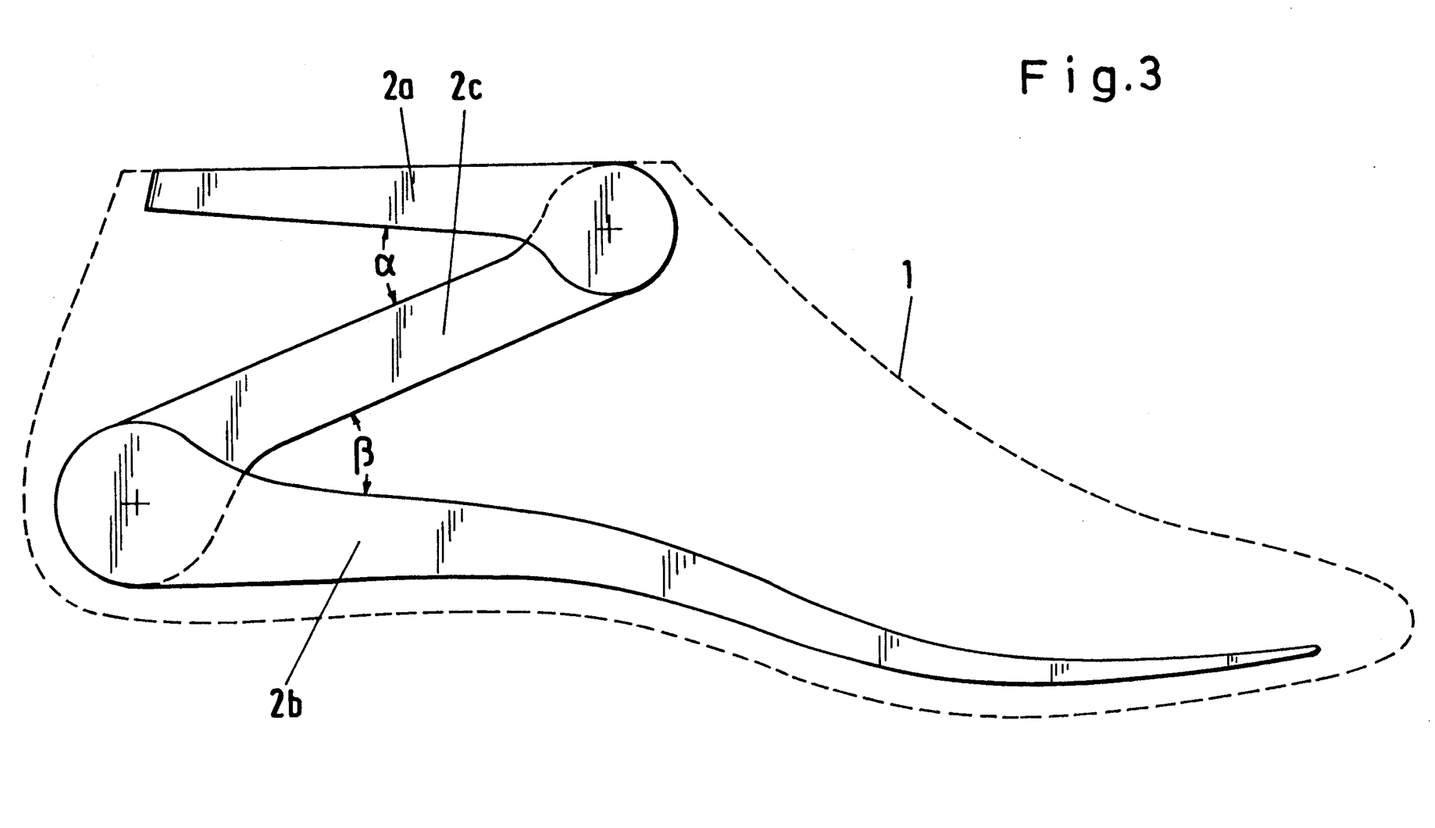
FIG. 3 shows a prosthetic foot having a foot insert of three-part construction.

While FIG. 1 shows an unstructured integral foot insert 2, FIG. 2 illustrates a foot insert 2 of two-part construction, the top section 2a of which is connected, as appropriate, in an articulated manner to the top end of the oblique Z-bar 2c. FIG. 3 shows a foot insert 2 of three-part construction, the two sections 2a, 2b of which are connected, as appropriate, in an articulated manner to the oblique Z-bar 2c.

Figure 4:
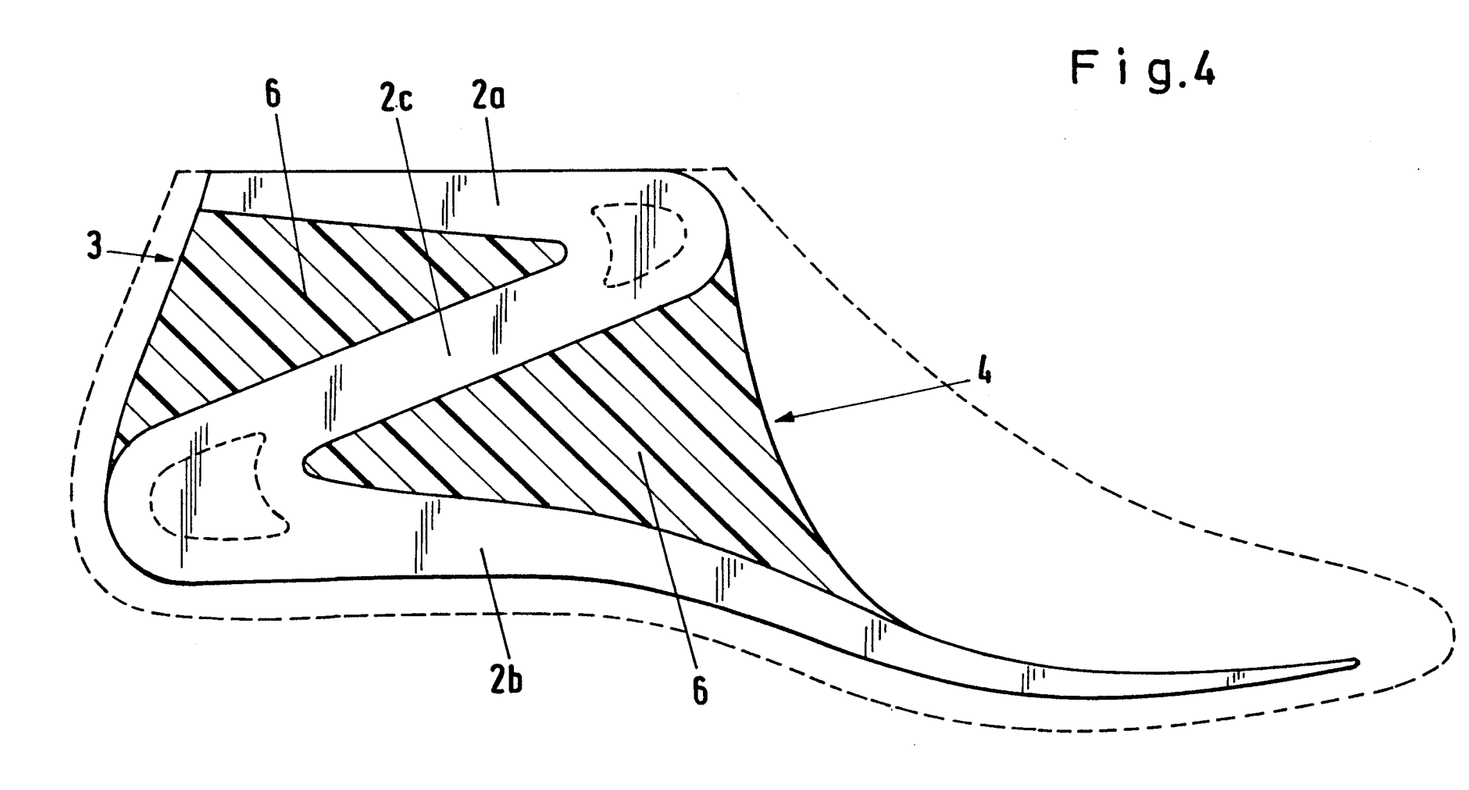
FIG. 4 shows a prosthetic foot having a foot insert according to FIG. 1, the rear and front wedge-shaped cavities of which are filled with a resilient substance.
Figure 5:
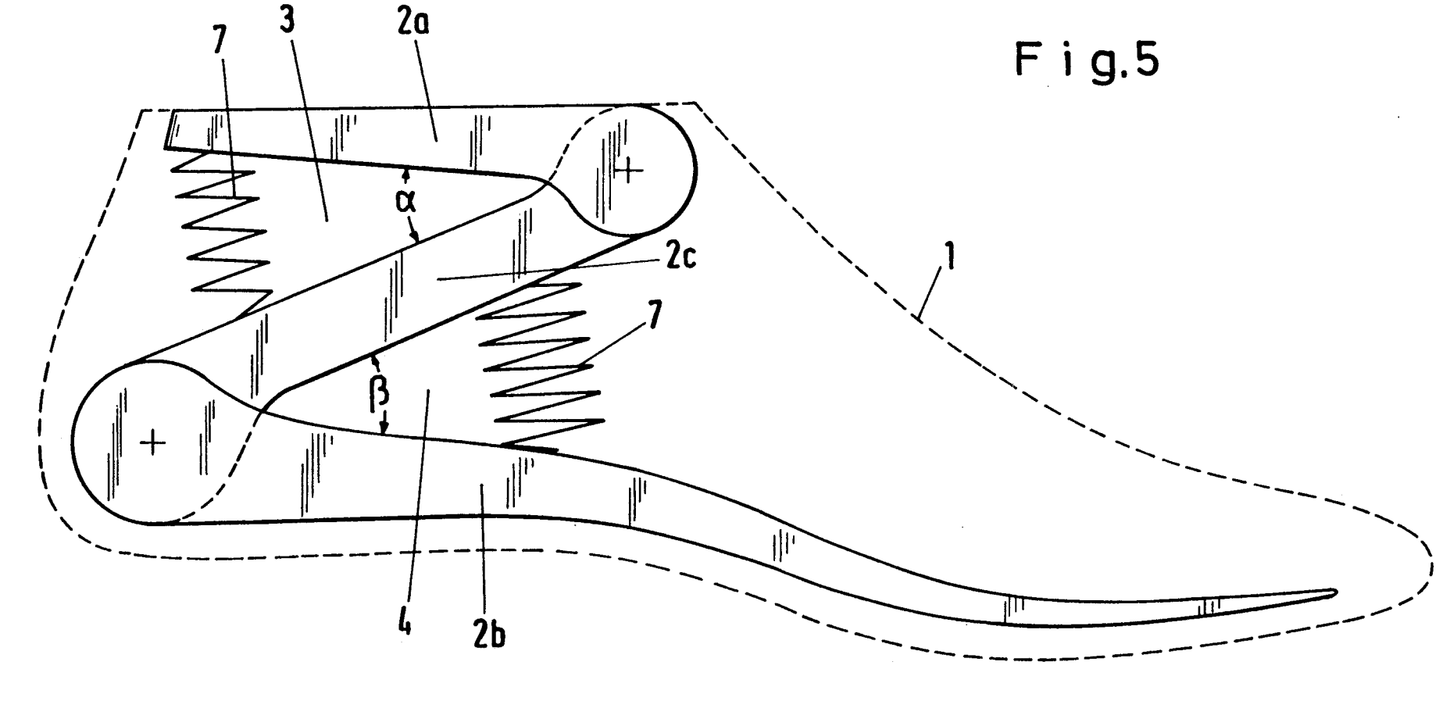
FIG. 5 shows a prosthetic foot having a foot insert according to FIG. 3, in the wedge-shaped cavities of which compression springs are arranged.
Figure 6:
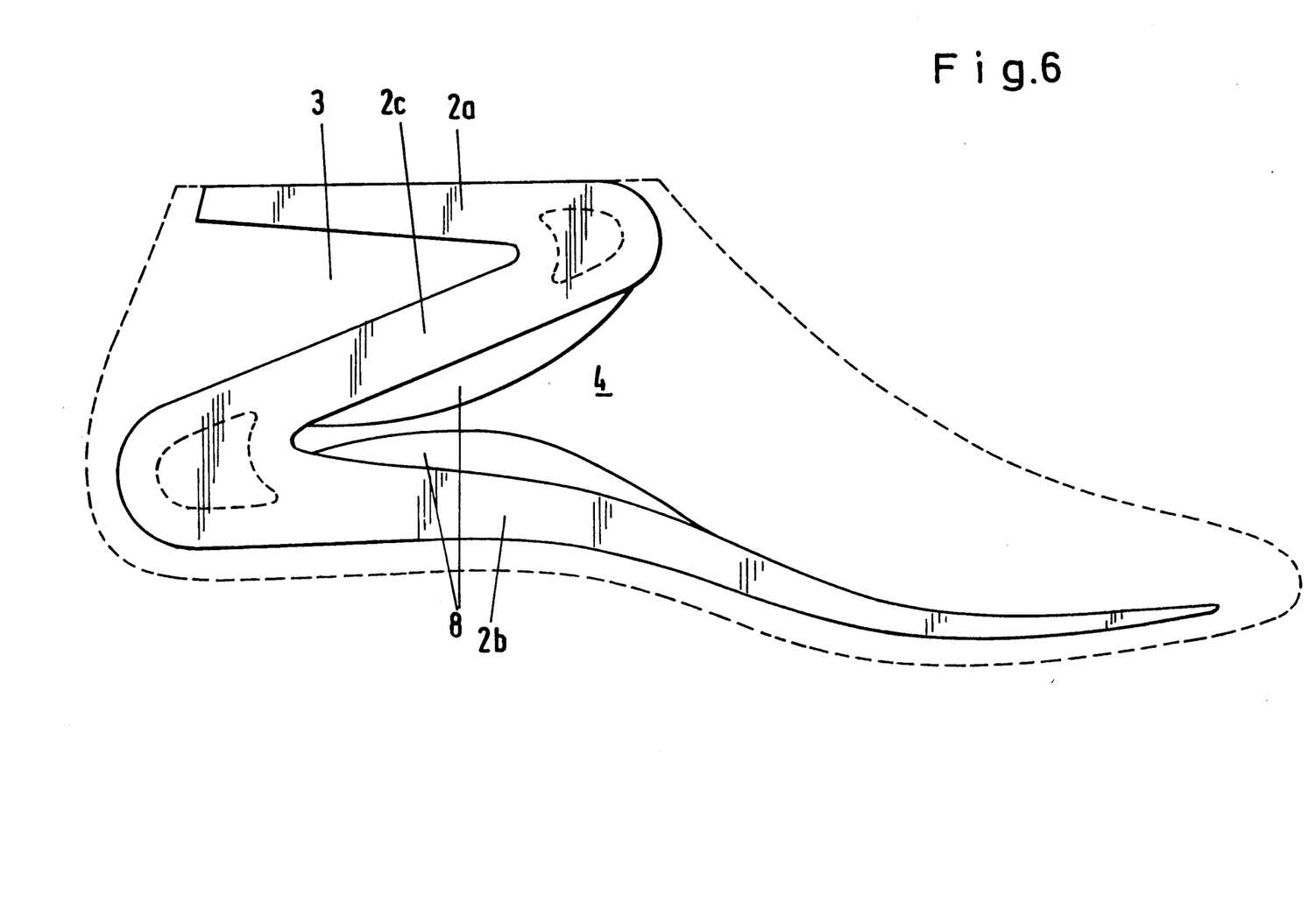
FIG. 6 shows a prosthetic foot having a foot insert according to FIG. 1, which is provided with additional support profiles

While the spring characteristics in the embodiments illustrated in FIGS. 1 to 3 are solely determined by the Z-shaped foot insert 2, FIGS. 4, 5 and 6 show various exemplary embodiments of the said spring characteristics being achieved in interaction with the Z-shaped foot insert 2 by additional resilient components which are arranged in at least one of the two wedge-shaped cavities 3, 4. In the example according to FIG. 4, the additional resilient components are formed by a resilient substance 6 which fills the two cavities 3,4. In the exemplary embodiment according to FIG. 5, the additional resilient components are compression springs 7 while, in the proposal according to FIG. 6, the additional resilient components are provided by separate or integrated support profiles 8 on the oblique Z-bar 2c and on the bottom section 2b of the foot insert 2. These support profiles 8 are arranged in the front wedge-shaped cavity 4.

Figure 7:
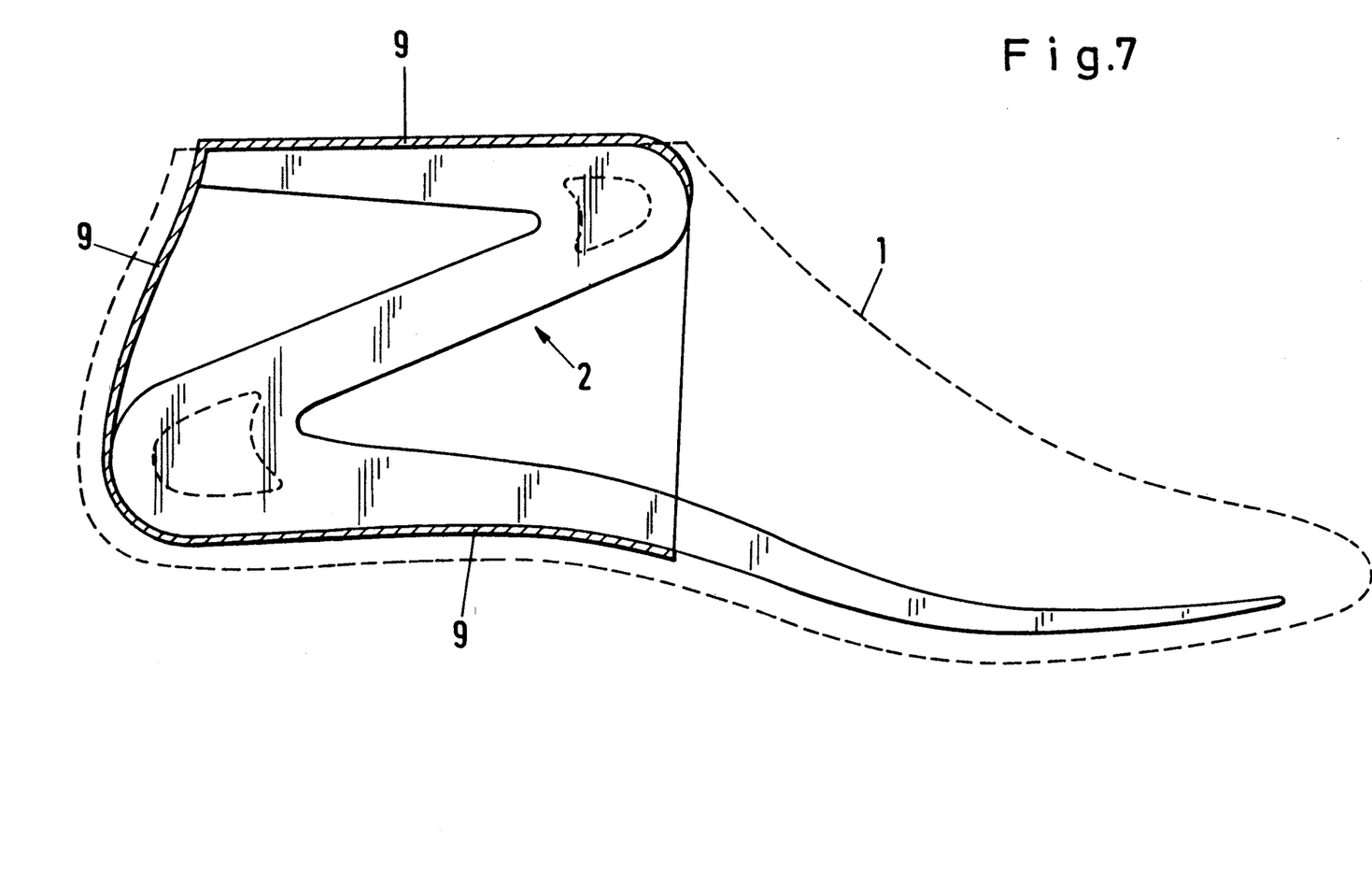
FIG. 7 shows a foot prosthesis having a foot insert according to FIG. 1 with a sock-like covering.

FIG. 7 shows an embodiment according to FIG. 1, the foot insert 2, however, being provided with a sock-like covering 9, by means of which the swivel range of the two sections 2a, 2b of the Z-shaped foot insert 2 is delimited in the sense of an enlargement of the top angle $\alpha$ and of the bottom angle $\beta$.

I claim:

1. A prosthetic foot having a front part including a toe section, a longitudinal part rearward of said front part, a top edge for non-articulate connection of said prosthetic foot to an artificial leg and a resilient foot insert located inside said prosthetic foot for receiving and transmitting stresses, said resilient foot insert comprising:

a top horizontal section forming said top edge;

a bottom horizontal section of more extended length than said top section having a free end extending into said toe section of said prosthetic foot for providing a high degree of elasticity for said front part of said prosthetic foot and a high degree of energy storage capacity when said front part of said prosthetic foot is stressed; and an oblique Z-bar section joining said top section and said bottom section in said longitudinal part of said foot to form an approximately Z-shaped construction;

said top section and said bottom section, respectively with said oblique section, enclosing a top angle forming a top rear wedge-shaped cavity and enclosing a bottom angle forming a bottom front wedge-shaped cavity;

said top section, said bottom section, and said oblique section together enabling at least one of plantar flection, dorsal flection, and axial compression for said prosthetic foot;

said plantar flection occurring as said top angle is reduced in a plane perpendicular to a pelvis of a wearer and parallel to a direction of walking;

said dorsal flection occurring as said bottom angle is reduced;

said axial compression occurring as both said top angle and said bottom angle are reduced by deformation and movement perpendicular to a plane of said perpendicular foot.

2. A prosthetic foot according to claim 1, characterized in that said top section of said foot insert can be twisted in a horizontal plane relative to said bottom section for allowing torsion and rotation of said prosthetic foot about a vertical axis.

3. A prosthetic foot according to claim 1, characterized in that said top section of said foot insert can be twisted in a frontal plane lying transversely and perpendicular in relation to said direction of walking relative to said bottom section for adaption to transverse inclinations in relation to said direction of walking.

4. A prosthetic foot according to claim 1, characterized in that resilient properties or spring characteristics, determining a force/path characteristic and angle/-movement characteristic of swivel movements and deformations of said foot, are solely determined by said foot insert.

5. A prosthetic foot according to claim 4, characterized in that separate support profiles are provided on said foot insert.

6. A prosthetic foot according to claim 5, characterized in that a contact point between two of said sections is separated by said support profiles under increasing stress.

7. A prosthetic foot according to claim 4, characterized in that integrated support profiles are provided on said foot insert.

8. A prosthetic foot according to claim 7, characterized in that a contact point between two of said sections is separated by said support profiles under increasing stress.

9. A prosthetic foot according to claim 1, characterized in that spring characteristics of said foot are achieved in interaction of said foot insert with additional resilient components arranged in at least one of said wedge-shaped cavities.

10. A prosthetic foot according to claim 9, characterized in that said additional resilient components are compression springs.

11. A prosthetic foot according to claim 9, characterized in that said additional resilient components are formed by a resilient substance filling at least one of said cavities.

12. A prosthetic foot according to claim 1, characterized in that a bottom profile of said bottom horizontal section corresponds to a profile of an underside of said foot.

13. A prosthetic foot according to claim 1, characterized by a device delimiting a swivel range of said top and bottom sections relative to an enlargement of said top and bottom angles.

14. A prosthetic foot according to claim 1, characterized in that said foot insert is of unitary integral construction.

15. A prosthetic foot according to claim 1, characterized in that said foot insert is of a two-part construction, with said top section being connected to a top end of said oblique Z-bar section.

16. A prosthetic foot according to claim 1, characterized in that said foot insert is of three-part construction with said top section and said bottom section being connected to said oblique Z-bar section.

17. A prosthetic foot according to claim 1, characterized in that said prosthetic foot comprises a foot-shaped foam structure embedding all said sections.

18. A prosthetic foot according to claim 1, characterized in that said prosthetic foot comprises a cosmetic cover enclosing all said sections.

* * * * *